(12) United States Patent
Burnett et al.

(10) Patent No.: US 10,610,134 B2
(45) Date of Patent: Apr. 7, 2020

(54) METHODS AND DEVICES FOR ANALYTE SENSING IN POTENTIAL SPACES

(71) Applicant: TheraNova, LLC, San Francisco, CA (US)

(72) Inventors: Daniel R. Burnett, San Francisco, CA (US); Evan S. Luxon, Omaha, NE (US)

(73) Assignee: TheraNova, LLC, San Francisco, CA (US)

( * ) Notice: Subject to any disclaimer, the term of this patent is extended or adjusted under 35 U.S.C. 154(b) by 0 days.

(21) Appl. No.: 15/629,337

(22) Filed: Jun. 21, 2017

(65) Prior Publication Data
US 2017/0281062 A1    Oct. 5, 2017

Related U.S. Application Data

(63) Continuation of application No. PCT/US2015/065387, filed on Dec. 11, 2015.

(60) Provisional application No. 62/102,528, filed on Jan. 12, 2015, provisional application No. 62/098,950, filed on Dec. 31, 2014.

(51) Int. Cl.
A61M 5/14       (2006.01)
A61B 5/145      (2006.01)
A61B 5/00       (2006.01)
A61B 5/1459     (2006.01)

(52) U.S. Cl.
CPC ........ A61B 5/14532 (2013.01); A61B 5/0031 (2013.01); A61B 5/1459 (2013.01); A61B 5/14507 (2013.01); A61B 5/4839 (2013.01); A61B 5/6852 (2013.01); A61B 5/6867 (2013.01); A61B 5/6858 (2013.01); A61B 5/6874 (2013.01)

(58) Field of Classification Search
CPC . A61B 5/14532; A61B 5/4839; A61B 5/1459; A61B 5/14507; A61B 5/6852; A61B 5/6867; A61B 5/0031; A61B 5/6874; A61B 5/6858
See application file for complete search history.

(56) References Cited

U.S. PATENT DOCUMENTS

| | | |
|---|---|---|
| 4,557,724 A | 12/1985 | Gregonis et al. |
| 4,581,020 A | 4/1986 | Mittleman |
| 4,861,341 A | 8/1989 | Woodburn |
| 5,100,392 A | 3/1992 | Orth et al. |
| 5,328,465 A | 7/1994 | Kratoska et al. |
| 5,637,088 A | 6/1997 | Wenner et al. |
| 5,995,860 A | 11/1999 | Sun et al. |
| 6,039,712 A | 3/2000 | Fogarty et al. |
| 6,122,536 A | 9/2000 | Sun et al. |

(Continued)

Primary Examiner — Amber R Stiles
(74) Attorney, Agent, or Firm — Levine Bagade Han LLP

(57) ABSTRACT

Use of the peritoneal space provides a more direct tracking of blood glucose, capturing faster glucose kinetics, avoiding membrane/encapsulation effects, having less lag time and lag time variability, and eliminating the effect of variations in skin temperature, cardiac output, and body position during sleep. A peritoneal sensor system may be implanted within the peritoneal space and may generally include a sensor/sampler portion, which is implanted in the peritoneal space, and a control portion/controller, which may be implanted elsewhere, such as subcutaneously, or may be external to the patient.

18 Claims, 16 Drawing Sheets

(56) References Cited

U.S. PATENT DOCUMENTS

| | | | |
|---|---|---|---|
| 6,254,586 B1 * | 7/2001 | Mann | A61B 5/14865 |
| | | | 206/365 |
| 6,343,225 B1 | 1/2002 | Clark | |
| 6,471,689 B1 | 10/2002 | Joseph et al. | |
| 6,702,857 B2 | 3/2004 | Brauker et al. | |
| 6,815,186 B2 | 11/2004 | Clark | |
| 7,018,336 B2 | 3/2006 | Enegren et al. | |
| 7,056,316 B1 | 6/2006 | Burbank et al. | |
| 7,228,160 B2 * | 6/2007 | Haight | C12Q 1/54 |
| | | | 600/316 |
| 7,247,138 B2 | 7/2007 | Reghabi et al. | |
| 7,351,233 B2 | 4/2008 | Parks | |
| 7,613,491 B2 | 11/2009 | Boock et al. | |
| 7,736,309 B2 | 6/2010 | Miller et al. | |
| 8,038,666 B2 | 10/2011 | Triplett et al. | |
| 8,050,731 B2 | 11/2011 | Tapsak et al. | |
| 8,147,455 B2 | 4/2012 | Butts et al. | |
| 8,292,808 B2 | 10/2012 | Miller et al. | |
| 8,543,184 B2 | 9/2013 | Boock et al. | |
| 2003/0125613 A1 * | 7/2003 | Enegren | A61B 5/14532 |
| | | | 600/347 |
| 2008/0039820 A1 | 2/2008 | Sommers et al. | |
| 2009/0030435 A1 | 1/2009 | Burnett et al. | |
| 2009/0254037 A1 * | 10/2009 | Bryant, Jr. | A61M 5/142 |
| | | | 604/151 |
| 2010/0280117 A1 | 11/2010 | Patrick et al. | |
| 2011/0196195 A1 | 8/2011 | Raven et al. | |
| 2012/0136343 A1 | 5/2012 | Burnett | |
| 2013/0079608 A1 | 3/2013 | Miller et al. | |
| 2013/0289540 A1 * | 10/2013 | Zeltser | A61M 1/28 |
| | | | 604/891.1 |
| 2014/0378791 A1 | 12/2014 | Dehennis et al. | |
| 2014/0378792 A1 * | 12/2014 | Krimsky | A61M 16/0427 |
| | | | 600/310 |
| 2015/0157248 A1 | 6/2015 | Brauker et al. | |

\* cited by examiner

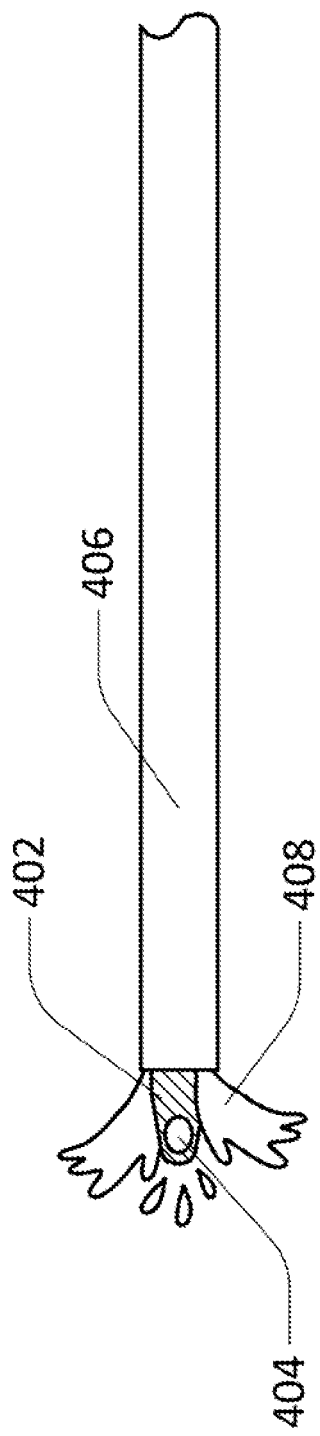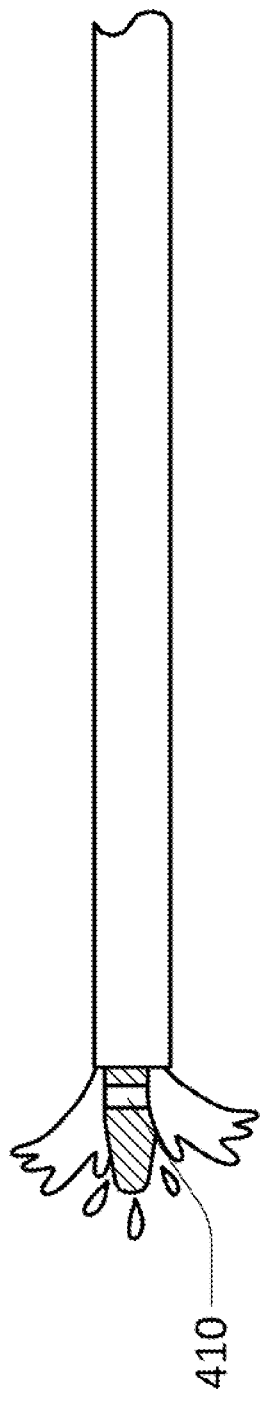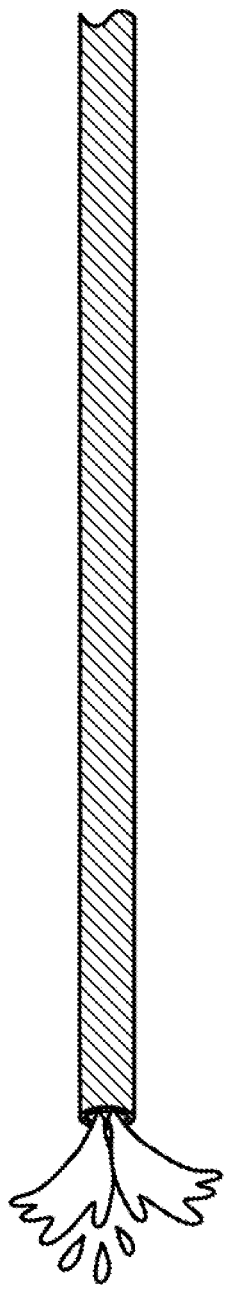

Sample raw data from an intravenous glucose change in pig

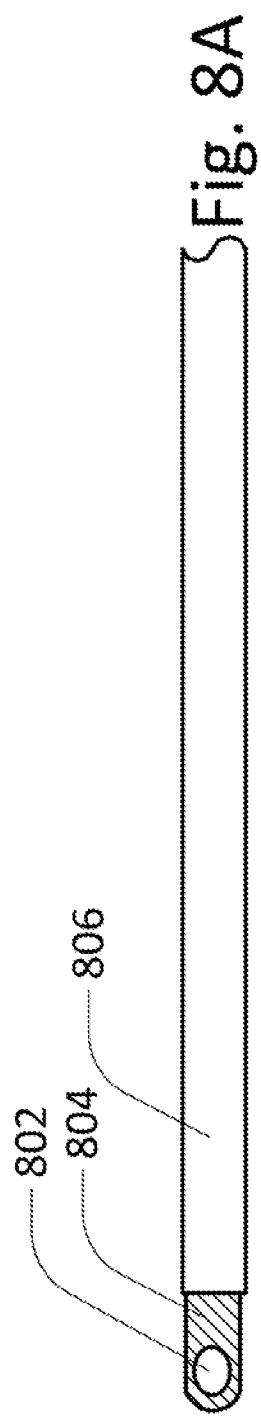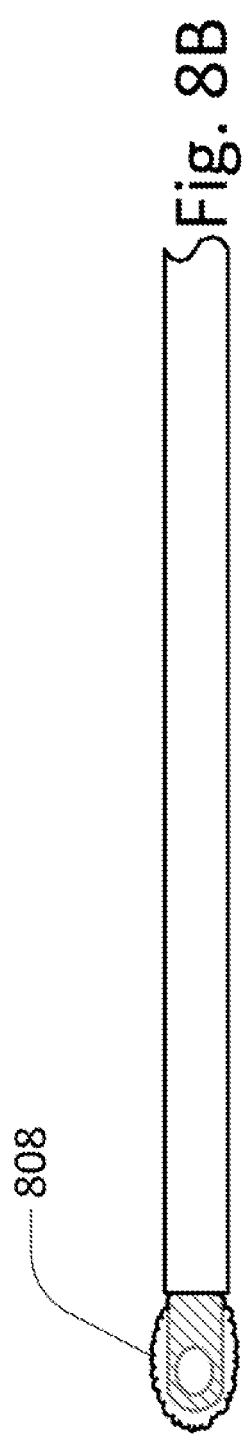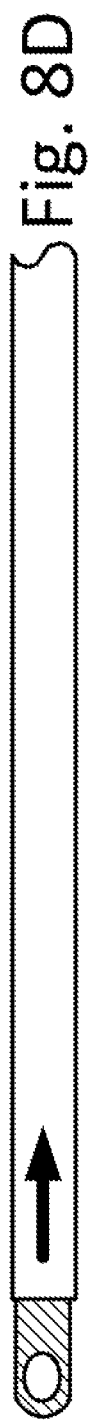

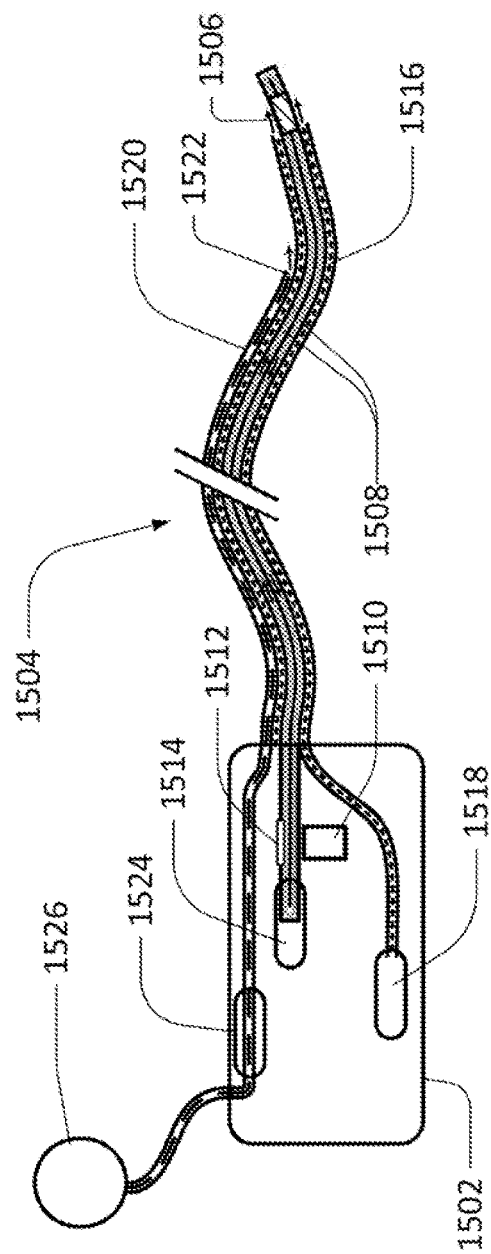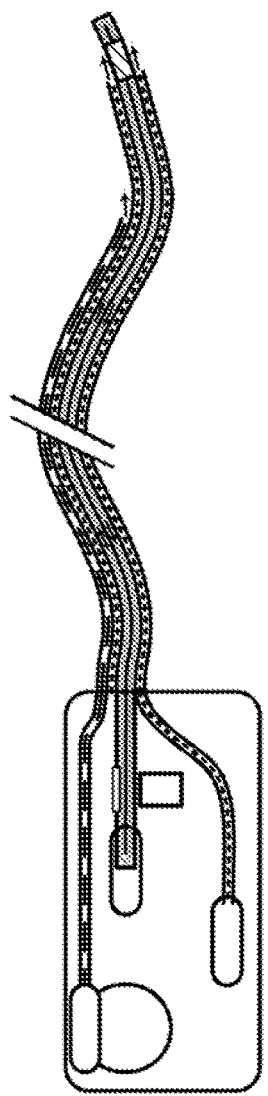

METHODS AND DEVICES FOR ANALYTE SENSING IN POTENTIAL SPACES

CROSS-REFERENCE TO RELATED APPLICATIONS

This application is a continuation of International Application No. PCT/US20151065387 filed Dec. 11, 2015, which claims the benefit of priority to U.S. Provisional Application Nos. 62/098,950 filed Dec. 31, 2014 and U.S. Provisional Application No. 62/102,528 filed Jan. 12, 2015, each of which is incorporated herein by reference in its entirety.

FIELD OF THE INVENTION

The present invention relates to the field of continuous biochemical monitoring systems. More specifically, the present invention relates to continuous glucose measuring devices with minimal lag.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Diabetes is a group of diseases characterized by high levels of blood glucose resulting from defects in insulin production, insulin action, or both. Diabetes is the leading cause of blindness in people ages 20 to 70 and is sixth leading cause of death in the United States. Overall, the risk for death among people with diabetes is about 2 times that of people without diabetes. The disease often leads to other complications such as kidney, nerve and heart disease and strokes. It is the leading cause for non-traumatic amputations and kidney failure.

Diabetes is reaching epidemic proportions in the United States. There are approximately 18.2 million people in the United States, or 6.3% of the population, who have diabetes. While an estimated 13 million have been diagnosed with diabetes, 5.2 million people (or nearly one-third) are unaware that they have the disease. Furthermore, diabetes is one of the most common chronic diseases in children and adolescents; about 151,000 people below the age of 20 years have diabetes.

Diabetics must diligently monitor the glucose level in their blood. Blood glucose levels should be maintained between 80 to 1.20 mg dl before meals and between 100-140 mg/dl at bedtime. Self-monitoring of blood glucose permits diabetics to know their blood sugar level so they can adjust their food, insulin, or activity level accordingly. Improved glucose control can forestall, reduce, or even reverse some of the long-term complications of diabetes.

The gold standard for testing blood glucose is the measurement of glucose in a plasma sample obtained from a vein. A drop of blood is placed on a small window in a test strip. Blood glucose acts as a reagent in a chemical reaction that produces a color change or generates electrons. The color change is detected by a reflectance-meter and reported as a glucose value. Alternatively, the electrons generated in the reaction are detected as an electrical current and reported as a glucose value.

Problems with these types of glucose measuring devices include the requirement of a drop of blood for each test (normally acquired through a prick of the finger). The blood sampling can be painful and cause calluses to form. It also increases the risk for warts and infections. The acute discomfort associated with this presents the largest barrier to life-saving blood glucose control.

Minimally invasive technologies currently include the GlucoWatch Biographer (no longer sold) and the Guardian® (registered trademark of Medtronic Minimed, Inc.) Continuous Glucose Monitoring System.

The GlucoWatch Biographer uses reverse iontophoresis, which involves applying an electrical microcurrent to the skin. The current pulls sodium through the intact skin, water follows sodium and water pulls glucose with it. The glucose concentration in this fluid is proportionate to the concentration in blood.

However, there are several problems with this technology. There is a lag time of 20 minutes before a blood glucose value can be reported. The concentration of glucose in the fluid is only $\frac{1}{1,000}$ of glucose in the blood. A mild skin discomfort last for a few minutes when the device is first applied to the skin. The device is intended for use only by adults (age 18 and older) with diabetes. It is intended to supplement, not replace, standard borne blood glucose monitoring devices. The user also has to calibrate the Gluco Watch Biographer with a blood glucose value measured on a traditional, i.e. "fingerstick," monitor. Thus a standard (invasive) blood glucose monitor is still required.

The Guardian® Continuous Glucose Monitoring System is designed to automatically and frequently monitor glucose values in subcutaneous interstitial fluid (ISF). It measures ISF glucose every five minutes and it has a hypoglycemia alert. Once inserted, the sensor is virtually painless, but it requires entry of glucose readings from a standard monitor at least twice a day in order to calibrate the sensor. Furthermore, the readings from this monitor lag the actual blood glucose values by 15-20 minutes potentially resulting in over or under dosing of insulin.

Other marketed devices include a subcutaneously inserted continuous glucose monitor which functions for several days before requiring replacement. These devices, though, measure interstitial blood glucose which frequently lags blood glucose by 15 minutes or more.

This lag time is suboptimal (more manageable lag times are in the 5-10 minute range). More importantly, the lag times for glucose measurements using subcutaneous sensors is not consistent. As a result, no one control algorithm can be used to create a closed-loop system. The inter- and intra-sensor variability in lag time is too great (5-30 minutes according to some reports) and doesn't apply to each sensor the same way or even apply to the same sensor during certain physiological situations.

Subcutaneous glucose sensors are generally placed at least weekly in the subcutaneous space. A sensor placed one week may be placed near a capillary bed (lag time 5-10 min while the sensor implanted a week later may be placed against a muscle fiber or fat tissue (30 minute or greater lag time). Therefore, the same control algorithm will not work adequately for both sensor placements. With respect to intra-sensor variability, many conditions affect blood flow to the submucosa of the skin. Cold temperature, for example, will drastically impact blood flow to the skin, and therefore have an effect on sensor readings. Sleeping also potentially impacts blood flow, and therefor subcutaneous sensor readings. Significant intra-sensor variability may exist between sleeping lag times and waking lag times. This variability may be due to episodes of severe nocturnal hypoglycemia.

SUMMARY OF THE INVENTION

The intraperitoneal (IP) space has been shown to have more effective, faster insulin delivery and faster glucose sensing kinetics than the subcutaneous space. Various, anatomical locations have been evaluated for blood glucose measurements, such as saliva and tears, and have been deemed inadequate for a closed, loop system due to latent lag times and interferences. The peritoneum, a thin transparent membrane that lines the walls of the abdominal cavity, contains the abdominal organs, and the fluids within the peritoneum are constantly exchanged by blood exudate. By comparison, subcutaneous tissues are located just below the skin surface and experience much lower blood perfusion rates. The IP space provides superior kinetics and a better medium for real-time glucose measurement.

Use of the peritoneal space provides a more direct tracking of blood glucose, capturing faster glucose kinetics, avoiding membrane/encapsulation effects, having less lag time and lag time variability, and eliminating the effect of variations in skin temperature, cardiac output, and body position during sleep. It would be implanted in an outpatient surgical center in a procedure similar to implantation of a peritoneal dialysis catheter. 2-fold faster glucose sensing kinetics can be achieved by placing a continuous glucose monitor in the intraperitoneal space versus the subcutaneous space. Sensing kinetics and sensor encapsulation are main factors contributing to accuracy and reliability of continuous blood glucose monitoring.

The peritoneal sensor system disclosed herein overcomes the inter- or intra-sensor lag time variabilities due to the consistent turnover of peritoneal fluid under most normal circumstances. Another potential advantage is the one-tune placement of the device in a protected and/or fixed position within the peritoneal cavity. In addition a cleaning feature may be incorporated into the device to decrease the impact of fibrotic ingrowth and biofilm formation on the sensor. The present invention provides shorter tag times and better control of analyte/glucose measurements, and also provides a consistency that is critical to closed-loop control of blood glucose levels, especially when coupled with an insulin pump. Insulin may be delivered to the peritoneal space as well, or it may be delivered elsewhere, such as subcutaneously.

Potential spaces within the body experience a diminished immune response compared to that of the skin or subcutaneous spaces. Positioning a sensor within a potential space, for example, within the peritoneal cavity, rather than subcutaneously, reduces the immune response to the device. However, implanting a device more deeply within the body, and communicating with the device from outside the body can be challenging. The peritoneal sensor system disclosed herein overcomes these challenges and enjoys a reduced immune response, a longer implant life, and shorter lag times than current devices.

The peritoneal sensor system allows for the sensing or sampling component to be tunneled or place in a potential space with a catheter/tether connecting it to a controller/transmitter within the subcutaneous or pre-peritoneal space, or outside the body. This not only allows for data and power transmission from the controller to the sensor/sampling component, but also allows for easier retrieval and swapping of the sensor/sampling component with a minimally invasive procedure. Ideally the sensor/sampling component implant or swapping procedure can be performed over a guidewire. The sensor/sampling component may be detached from the controller and a replacement sensor/sampler may be reattached to the controller. In some embodiments, the sensor/sampler is accompanied by an insulin infusion catheter or lumen to provide not only the faster and more durable sensing benefit of the peritoneal space, but also the faster insulin absorption benefit of the peritoneal space.

Generally, the peritoneal sensor system may comprise a catheter having a distal tip which is tapered, and a sensor positioned within the tapered distal tip of the, catheter, wherein the sensor is configured to sense for a presence of one or more analytes when positioned within peritoneal fluid of a subject. A filter may be in fluid communication with the sensor may also be included, wherein the filter is permeable to the one or more analytes, as well as a controller in communication with the sensor and a port in fluid communication with the catheter and the sensor, wherein infusion of a fluid through the port flushes the sensor with the fluid.

In yet another embodiment, the peritoneal sensor system may comprise a catheter having a distal tip which is tapered, and the sensor configured to sense for a presence of one or more analytes when contacting peritoneal fluid of a subject. A controller in communication with the sensor may also be included, wherein the sensor is positioned within the controller, as well as a filter in fluid communication with the sensor, wherein the filter is permeable to the one or more analytes and a port in fluid communication with the catheter and the sensor, wherein infusion of a fluid through the port flushes the filter with the fluid.

In use, the sensor system may be used for detecting one or more analytes within a subject, generally comprising contacting peritoneal fluid within the subject via a distal tip of a catheter, where the distal tip is tapered to inhibit or reduce an ability of a fibrotic capsule from obtaining purchase, filtering the peritoneal fluid, wherein the filter is permeable to the one or more analytes, sensing for a presence of one or more analytes within the peritoneal fluid via a sensor, determining whether the one or more analytes are present within the peritoneal fluid via a controller in communication with the sensor, and infusing a fluid within the catheter such the fluid flushes the distal tip.

Any of the embodiments detailed herein can be used in any potential space, including, but not limited to, the pleural space, the cerebral spinal fluid space, the peritoneal space etc.

Any of the embodiments detailed herein may include a sensor in the potential space, and/or a sampler in the potential space. In some embodiments, a fluid/analyte sampler is in the potential space, and a sensor is in the controller which may be in the subcutaneous or pre-peritoneal space or external to the patient.

BRIEF DESCRIPTION OF THE DRAWINGS

FIGS. 4A-4C show some example embodiments that incorporate flushing.

FIGS. 8A-8D show embodiments which include mechanisms to clear fiber/fibrin and encapsulation FIGS. 9A-9D slows an embodiment which includes an expandable mesh-like, or cage-like, component.

FIG. 15 shows an embodiment of the peritoneal sensor system which uses spectroscopy or spectrophotometry.

FIG. 16 shows another embodiment which uses spectroscopy or spectrophotometry.

DETAILED DESCRIPTION OF THE INVENTION

The peritoneal sensor system generally includes a sensor 'sampler' portion, which is implanted in the peritoneal space, and a control portion/controller, which may be implanted elsewhere, such as subcutaneously, or may be external to the patient. Other functions which may be included include insulin delivery, sensor flushing, wireless communication, light spectroscopy, UV sterilization, analyte sampling, analyte circulation, logic, etc.

Figure 1:
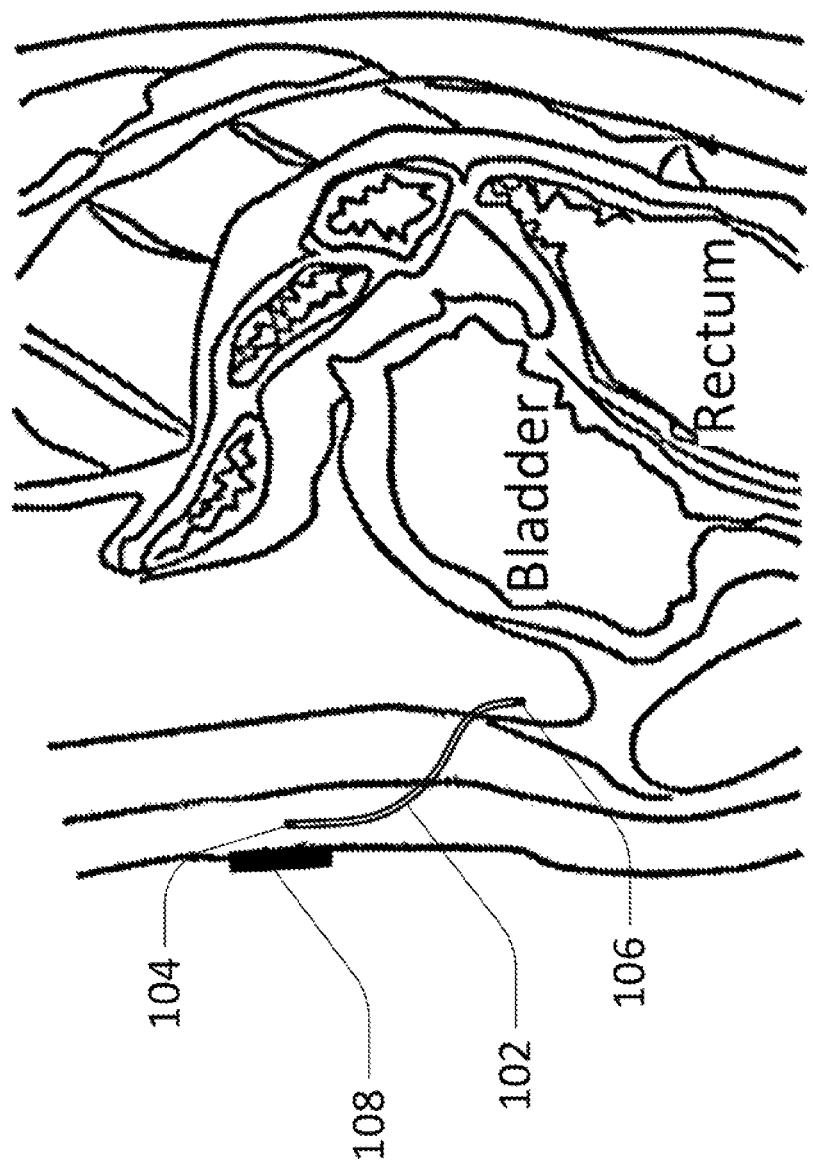
FIG. 1 shows an embodiment of the peritoneal sensor system with a catheter/tether which includes wireless communication.

FIG. 1 shows an embodiment of the peritoneal sensor system with a tether/catheter which includes wireless communication. The embodiment of the peritoneal sensor system shown here includes catheter/tether 102 including subcutaneous antenna 104 on one end, and sensor portion 106 on the other end. For example, the sensor may sense the presence of glucose. This allows the sensor portion to communicate with external transmitting controller 108 where the sensor portion has low power requirements despite its position deep within the body. This design may incorporate an anchoring cuff or tunnel, for example, a cuff made of Dacron, to allow for tissue ingrowth and subsequent anchoring of catheter/tether to the body to hold it in place. The anchoring cuff may be anchored to a thin biocompatible tube or tunnel through which the sensor/catheter/tether assembly may be inserted from the subcutaneous space into the peritoneal space.

When the sensor has reached the end of its useful life, the antenna end of the catheter/tether may be accessed under local anesthesia, the sensor/catheter/tether assembly may be removed from the biocompatible tube through gentle traction and another sensor slid into the tube to replace the expired sensor. This assures consistent and easy placement of the sensor portion within the peritoneal cavity. Placement may also be accomplished by threading a guidewire down the center of the sensor/catheter/tether assembly, removing the sensor/catheter/tether assembly, then threading a new sensor/catheter/tether assembly over the guidewire. In this last embodiment, the tube or tunnel and/or anchoring cuff may not be necessary due to the formation of a fibrotic tunnel for the replacement sensor/catheter/tether assembly to follow.

Figure 2:
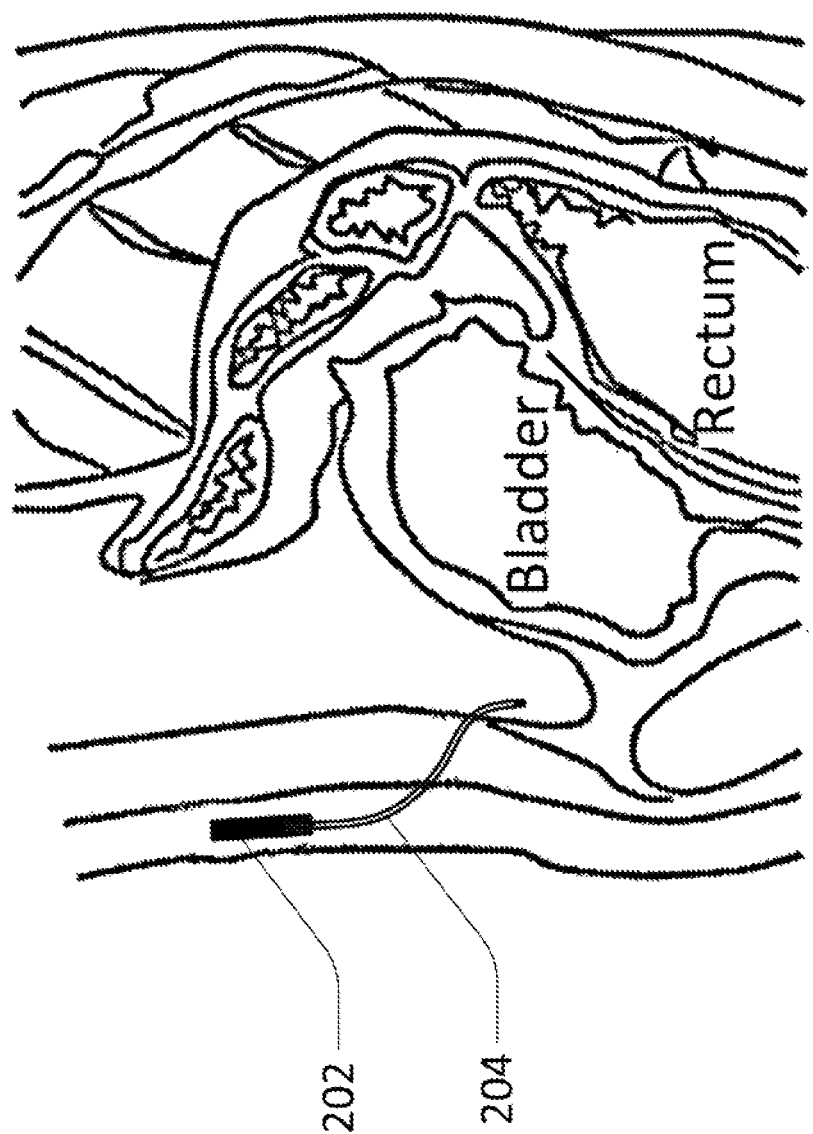
FIG. 2 shows another embodiment of the peritoneal sensor system.

FIG. 2 shows another embodiment of the peritoneal sensor system. The system detailed in this Figure includes implanted controller portion 202, shown here in the subcutaneous space. The controller portion may alternatively be in the peritoneal or pre-peritoneal space. In this embodiment, sensor/catheter/tether assembly 204 is connected to implanted controller portion 202. In this embodiment, the control portion in the subcutaneous space may provide automated intermittent flushing of the sensor portion and provides power to the sensor portion and may store/transmit any collected data. Alternatively, flushing, may be achieved manually or automatically via an implanted port using, a syringe or other infusion device. The sensor portion may also or alternatively be flushed/refilled by an external port. Any of the embodiments may also allow for automatic or manual infusion of insulin based on the glucose readings in the peritoneal space. Insulin may be infused/refilled similarly to the flushing solution Insulin and the flushing solution may be combined. The sensor/catheter/tether assembly may include a sensor, or it may simply sample fluid, causing it to flow to or past a sensor within the controller to determine the analyte concentration.

Figure 3:
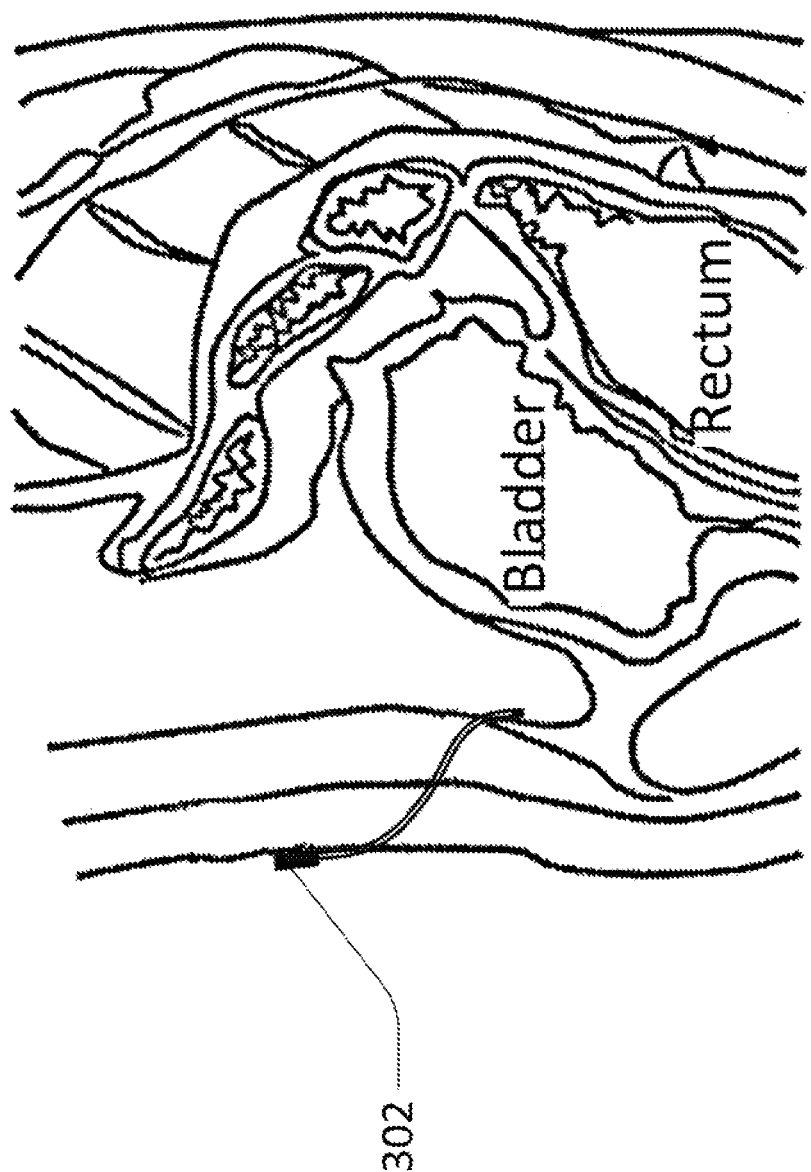
FIG. 3 shows an embodiment of the peritoneal sensor system with an externalized control portion.

FIG. 3 shows the use of an externalized control portion. In this embodiment, control portion 302 may be externalized and interface with the sensor/catheter/tether portion outside of the body. The system may also incorporate sensor flushing and/or insulin infusion and may incorporate one or more anchor cuffs to prevent infection tracking. In this embodiment, the external control portion of the system may be very small and include a small chip and a small battery to collect, store and transmit the signals of the sensor portion of the system. The external control portion may be less than 5 cc in volume and be relatively inconspicuous. The external control portion may also incorporate a small pump and a small insulin reservoir to provide a true artificial pancreas solution in a very low-profile design. All or part of the external control portion may be replaced and/or refilled on a daily, weekly or monthly basis to allow for a smaller, more compact profile.

The sensor portion may be replaced on a similar timeframe, or less frequently, to allow for a more stable signal over time. It the control portion (externalized or implanted) includes the ability to infuse insulin, the insulin may be infused at a site along the length of the tether/catheter that is in the peritoneal cavity, but is far enough away from the sensor to prevent signal disruption. For example, the insulin delivery exit may be about 0.5 cm to 1.5 cm from the sensor. Alternatively, the insulin may, itself, act as the flush for the sensor.

In any of the embodiments disclosed herein, any suitable sensing technology may be used, but ideally a sensor will be used that is both durable and resistant to micromotion and macromotion artifact. The sensor portion may include glycoenzymatic sensors with a membrane to prevent acute disruption of their surroundings. In some embodiments, the sensor portion includes a sensing modality that does not consume glucose such as infrared, raman spectroscopy, spectro-photometry, fluorescence (conA or boronate chemistry) or phosphorescence.

The terms, sensor, or sensing element, as disclosed herein, may also include a local or remote interface to a sensor. For example, a filter membrane which is permeable to glucose, but impermeable to other contaminates, may be used to filter fluid from the peritoneal cavity. The sensor in these embodiments may be in proximity to the filter membrane, or it may be remote to the filter membrane. For example, the filter membrane may be at the tip of the catheter assembly, but the sensor may be either at the proximal end of the catheter assembly, or in the control portion of the system. Alternatively the filter membrane may be in the controller or at the proximal end of the catheter. In these embodiments, a fluid column, or fluid reservoir, is in fluid communication with both the filter membrane, and the sensor.

In some embodiments, the sensor/catheter/tether assembly may incorporate an insulin infusion lumen and/or a flushing lumen to keep the sensor free of encapsulation. The flushing lumen may be intermittently flushed from an internal reservoir of fluid, fluid from the peritoneal cavity, or fluid from an external source. Flushing may be performed automatically or manually. FIGS. 4A-4C show some example embodiments that incorporate flushing. The distal end of the catheter/sensor assembly is designed to prevent a fibrotic capsule from obtaining purchase and may therefore be either consistent in diameter or decreasing in diameter (moving proximally, to distally) and smooth, i.e. free of any trapped spaces, or indentations, to prevent trapping of fibrin and to allow a flush to readily remove any capsule forms. In other words, the tip of the catheter may be tapered so it is smaller toward the distal tip. The tip of the catheter is preferably made from a material which inhibits cell ingrowth such as silicone or other suitable material. This tapered tip feature may be incorporated into any of the embodiments disclosed herein.

FIG. 4A shows distal end 402 of the catheter/sensor assembly. The catheter assembly includes sensor or sensor interface 404. Flushing fluid, such as saline, peritoneal fluid, insulin or other fluid 408 is flushed through the annular lumen between flushing sleeve 406 and the catheter assembly. Note that in this embodiment the distal tip of the catheter assembly is smooth, and decreasing in diameter (moving proximally to distally). This helps the forces supplied by the flushing action to remove any fibrin capsule. Although the flushing lumen shown here is annular, the flushing lumen may also be round or any other shape, and may be along one or more than one side of the catheter assembly. Insulin may be infused through the flushing lumen, or through a separate lumen. The distal opening of the insulin lumen may be proximal to, and spaced apart from, the sensor at the distal end of the catheter assembly. A separate insulin lumen is not shown here.

FIG. 4B shows another embodiment: of the peritoneal sensor system catheter assembly. In this embodiment, filter membrane 410 is shown. In this embodiment, filter membrane 410 may encircle the distal tip of the catheter assembly for maximum surface area exposure.

FIG. 4C shows an embodiment of the catheter assembly where the sensor is inside the lumen of the catheter assembly. In this embodiment, flushing may be performed through the same lumen as the lumen where the sensor resides.

In some embodiments of a flushing mechanism, the flushing solution may be used to flush the sensor portion to clear off encapsulation. In some embodiments of the sensor assembly described herein, the flushing fluid exits the flushing sleeve proximal to the sensing element and flushes the sensing element toward the tip, or distal end. Alternatively, the flushing solution may exit the tubing distal to the sensing element and flush the sensing element in the opposite direction, or proximally. Ensuring adequate fluid flow over the sensing element helps keep the sensing element clear and readings accurate and with minimal lag time. Flushing may occur continuously or intermittently.

Figure 5:
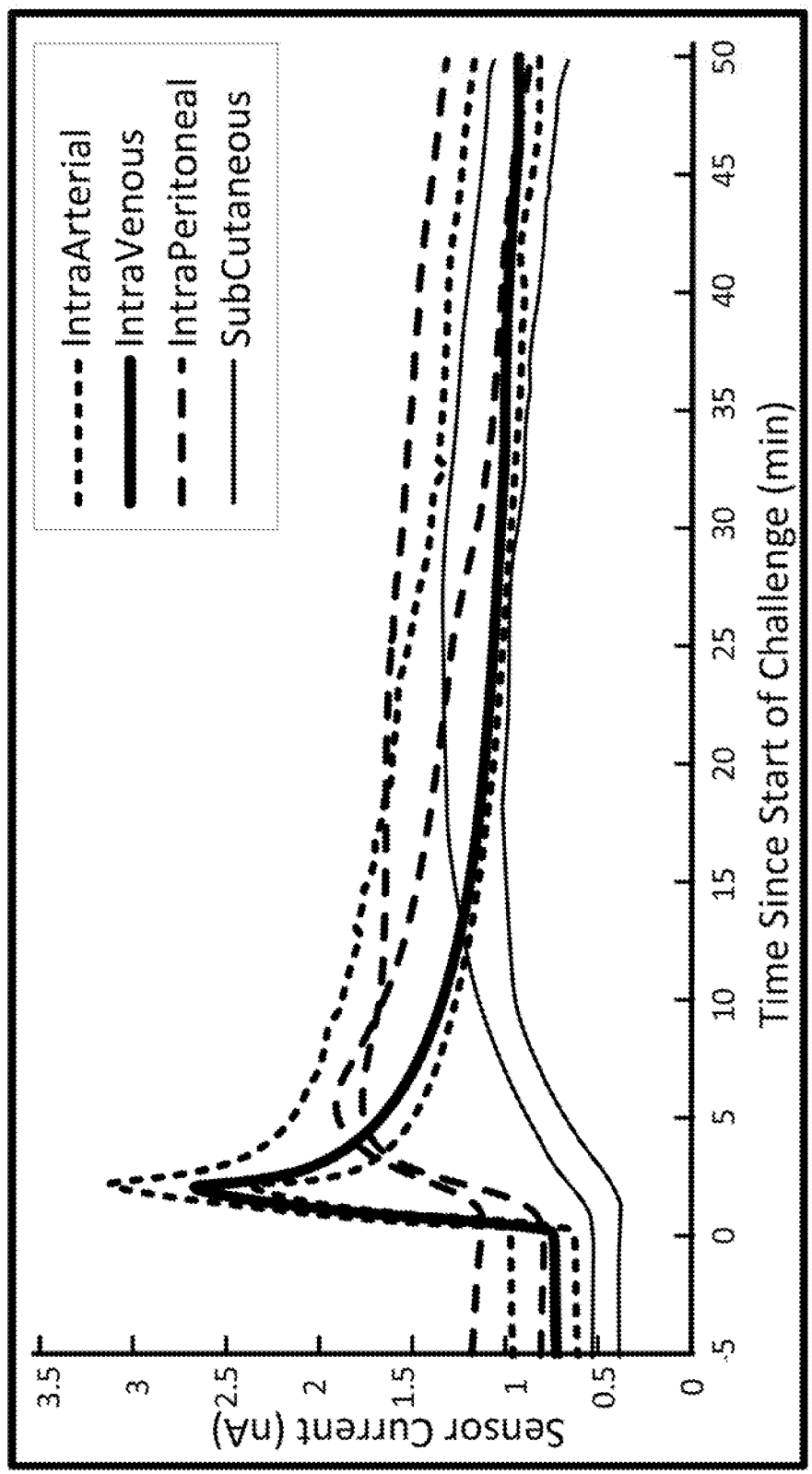
FIG. 5 shows the relative responsiveness of sensors implanted in the peritoneal cavity, subcutaneous space and in the intravenous space.

FIG. 5 shows the relative responsiveness of sensors implanted in the peritoneal cavity, subcutaneous space and in the intravenous space. The curves are shown following an Intravenous Glucose Tolerance Test (IVGTT). The sensor implanted in the peritoneal cavity resulted in a faster signal response than those implanted in the subcutaneous space. The response time of the sensor in the peritoneal cavity approached that of the intravenous sensor.

Micromotion and Noise Prevention

Dynamic changes in the environment immediately surrounding the sensor may cause sensor signal noise. These dynamic changes may be a result of the peristaltic motion moving the sensor and/or micro motion associated with the sensors. These motion artifacts may adversely affect the signal of enzyme based sensors which rely on stable gradients of glucose, oxygen and $H_2O_2$ in order to generate a nanoampere current which can be translated into a blood glucose reading. Shifts in this local environment may cause significant changes in the nanoampere current which may adversely affect the resulting blood glucose signal. The peritoneal sensor system may reduce signal noise in some embodiments by controlling the environment near the sensor, using multiple sensors, and/or using a sensor which does not consume glucose.

Controlling the Environment Near the Sensor

A semi permeable membrane, or filter membrane, or other material may be used to filter the fluid which comes in contact with the sensor. This allows fluid to flow in the area local to the sensor and allows analytes (such as glucose) to diffuse in and out of the membrane, while preventing contaminates from doing so. In other words, the semi permeable membrane has pores that allow glucose (or any specific analyte) to pass through the pores, but larger items in the fluid cannot pass through the membrane. Alternatively, the membrane may allow only specific items to pass through it based on other characteristics other than size, for example electric charge, shape, etc. This technique increases the stability of the sensor signal, and also reduces contaminating components of the analyte fluid. Using a thin membrane, that encourages local diffusion in and out of the membrane over the order of seconds to minutes, allows the signal to be sufficiently stabilized to allow for the acquisition of the required data with acceptable lag times. The membrane may be near the sensor, for example covering the sensor, or the membrane may be remote to the sensor, with fluid communication between the membrane and the sensor.

Filter membranes may be made out of any suitable material known in the art, including the materials disclosed in U.S. Pat. Nos. 8,543,184, 7,613,491, and 8,050,731, each of which is hereby incorporated by reference in its entirety. The filter membrane may be hydrophilic or hydrophobic.

Multiple Sensors

In another embodiment, a "web" or array of sensors may be dispersed within the peritoneal cavity, for example around the pancreas, to collect glucose concentration data from multiple locations within the peritoneal cavity. In this embodiment data is collected from multiple locations. These values obtained from the multiple sensors may be averaged and signal noise is reduced.

Sensors Which Don't Consume Glucose

Non-glucose consuming sensors are highly resistant to motion (both micromotion and the larger peristalsis-related motion) because they do not rely on detection of $H_2O_2$ in the local milieu of the sensor to maintain stability of readings. This type of sensor may include spectro-photometric, infrared, LED, raman spectroscopic, fluorescent or phosphorescent sensors or may rely on any other mechanism to detect glucose in a sample that does not consume the glucose or generate readings based on byproducts of an enzymatic reaction. The use of a non-enzymatic, non-glucose-consuming sensor in the peritoneal cavity generates stable readings with minimal signal tag times.

Encapsulation

Implanted sensors will become encapsulated over time once implanted and the signal lag time will lengthen if the sensor is not flushed or otherwise cleaned. This increasing lag time can be found in sensors in either the peritoneal and subcutaneous spaces, but is more extreme in the subcutaneous space. Encapsulation has also been found to be more rapid and more extreme in the upper quadrant of the peritoneal cavity than in the lower quadrant's (away from the omentum). Because of this, placing the sensor component in the pelvis (away from the omentum and liver) may be optimal. Alternatively, in the event that a patient has pelvic omentum, a method of catheter/sensor placement may be utilized which includes a procedure to tack the omentum up near the liver to keep the omentum away from the pelvic region.

In addition, we have discovered an unexpected finding during our intravenous glucose tolerance tests that indicate that during hyperglycemia (blood glucose >200 mg/dL) abnormally high glucose values were reported only in sensors in the upper quadrant of the peritoneal cavity. These values were in excess of the glucose values reported by capillary and plasma glucose. Conversely, the glucose readings of the pelvic peritoneal sensors tracked the readings of the capillary and plasma glucose readings more closely. Based on these data, it is possible that the liver "weeps" glucose into the peritoneal cavity when it is overwhelmed with hyperglycemia thereby creating falsely elevated glucose readings in sensors in that area. This could lead to excessive insulin administration which could be fatal. For this reason the sensor portion may not be placed in the traditional site of peritoneal cavity access for insulin infusion—the hepatic region.

In any system that senses glucose and delivers insulin, the glucose sensing may be more successfully accomplished at a distance away from the site of insulin delivery (which has traditionally been in the hepatic region). This may be accomplished with sensing in the pelvis and delivery of insulin in the hepatic region (a single dual lumen catheter or two single lumen catheters) or, alternatively, insulin delivery and glucose sensing both performed in the pelvis.

Figure 6:
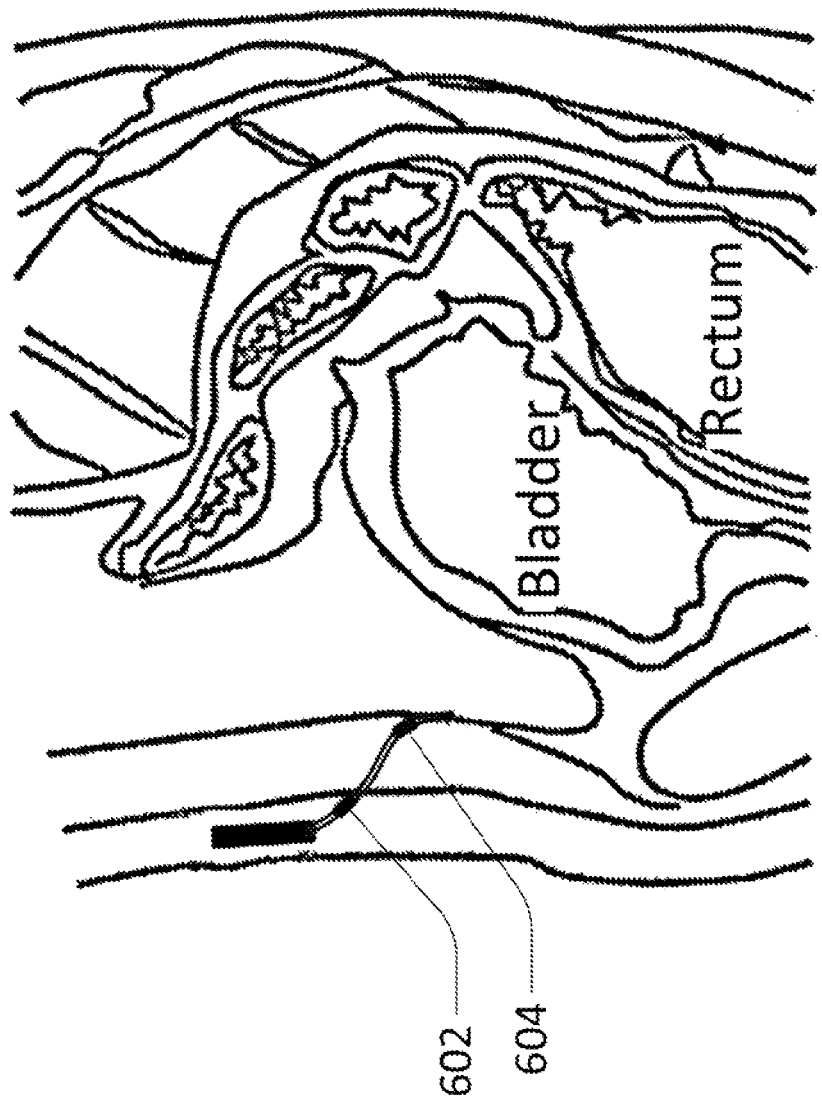
FIG. 6 shows another embodiment of the peritoneal sensor system.

In some embodiments of the peritoneal sensor system, the peritoneal catheter (or catheter in any other potential space), may lie along the wall of the cavity and not protrude significantly into the space. This may prevent issues with catheter kinking, catheter movement due to peristalsis or direct force from the organs, and catheter obstruction/erosion due to direct organ contact. The catheter portion of the present invention may be placed in the pelvis with a short section of the catheter being tunneled through the rectus sheath or preperitoneal space prior to entry into the peritoneal cavity (see FIG. 6). This allows for the catheter to be angled into the pelvis and away from the omentum to better ensure its continued patency and function. This placement can be used with either the analyte (such as glucose) sensor portion (or sampling portion) and/or drug (such as insulin) infusion portion of the system. These may be included on the same catheter or be separate catheters. Optional anchoring, or ingrowth, cuffs, 602 and 604, are shown in FIG. 6.

Figure 7:
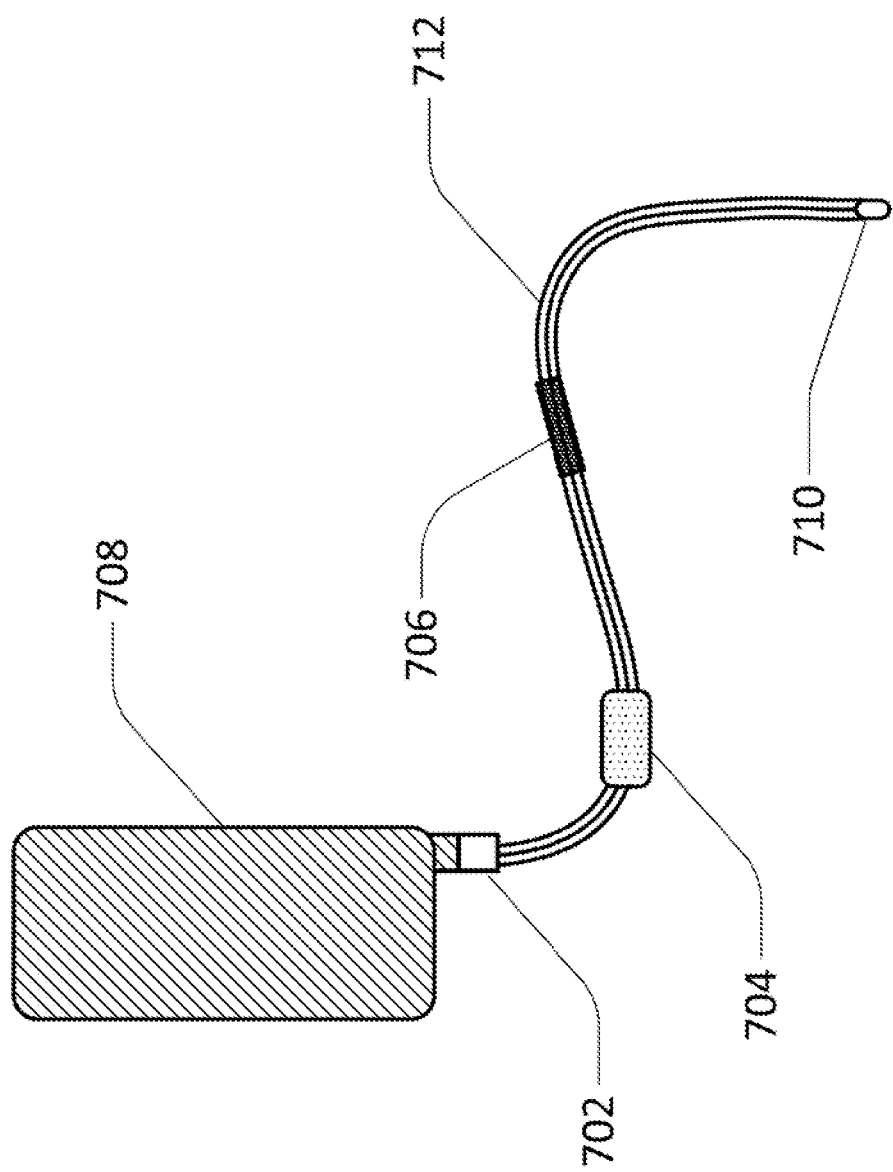
FIG. 7 shows an embodiment of the peritoneal sensing system with an anti-adhesion cuff.
Figure 9A:
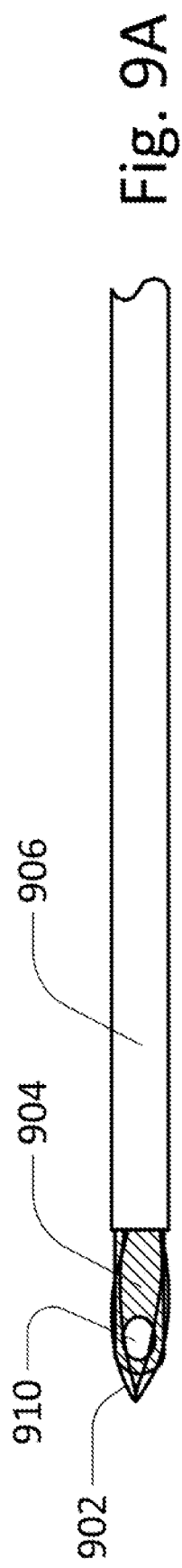
Figure 9B:
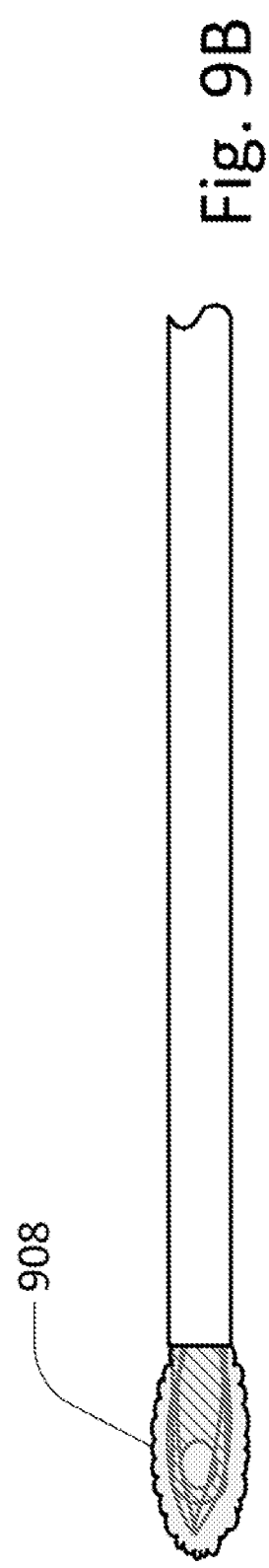
Figure 9C:
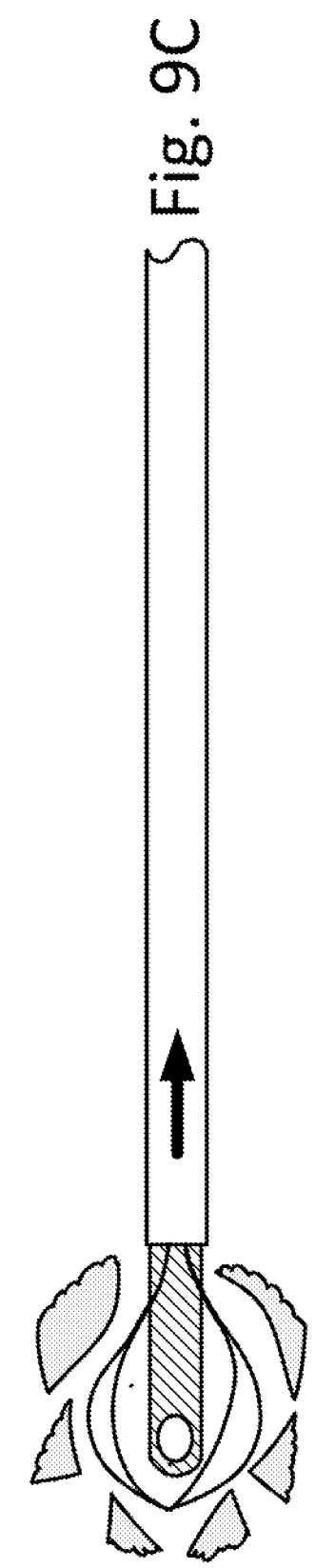
Figure 9D:
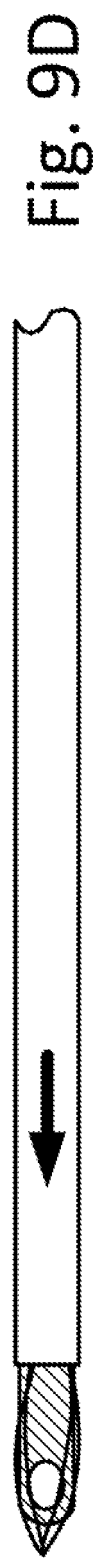

FIG. 7 shows an embodiment of the peritoneal sensing system with an anti-adhesion cuff. While all foreign bodies generate a foreign body response, different materials do so at different rates. For example, ePTFE of the appropriate pore size and silicone from a polished mold (or coated with PEG, albumin or other hydrophilic coatings) will be highly anti-adhesive. A short segment of anti-adhesion material, or an anti-adhesion cuff shown as 706, on sensing catheter 712 will create a weakness in any fibrin capsule overlying this site. This weakness will allow the capsule to break at this point and be flushed from the distal end of the catheter with a fluid infusion or flush. The diameter of the distal end of the catheter is preferably constant in size or decreasing in size, and smooth, so that the catheter has no ridges or crenellations that will allow a capsule to invade and take hold. Drugs or other additives may also be added to the anti-adhesive cuff.

Also shown in FIG. 7 is reversible connector 702, one or more ingrowth cuffs 704 to prevent tracking of any infection or fluid along the catheter and controller 708. Tip 710 of infusion/sensing/sampling catheter 712 will ideally be blunt, and possibly weighted. Catheter 712 may include an insulin infusion sheath. Catheter 712 may include sterilization elements including electric current, silver, an ultraviolet light source etc. A glucose sensor may travel alongside, or within an insulin infusion sheath. Fluid, such as a dialysate, may be circulated within a dual lumen catheter, or forced in and out of a single lumen catheter, and drawn over a sensor via a pump. The sensor may be at the tip of the catheter, or it may be anywhere along the catheter, or it may be within the controller. Peritoneal fluid may also be drawn into the catheter to pass over the sensor.

Other embodiments include additional mechanisms to clear fiber/fibrin and encapsulation. In one embodiment, the sensor body is assembled with an outer collar, or sleeve, that can be slid over the catheter body periodically to act as a wiper to physically remove any encapsulation growth 808, so that sensor 802 can function properly. See FIGS. 8A-8D. The collar/sleeve may run the length of sensor catheter 804, as shown here, or may be shorter than the sensing catheter, and controllable by moving catheter 804 relative to sleeve/cuff 806. The clearing action can be initiated by pulling the sensor assembly back while the collar stays in place or pushing the collar/sleeve forward while the sensor stays in place. This could be performed manually by the patient or via a hand pump. It could also be performed automatically using an air pump or motor actuation to push or pull the collar or sensor assembly.

FIG. 9 shows an embodiment which includes an expandable mesh-like, or cage-like, component comprised of thin gauge, wire (e.g. stainless steel or Nitinol). Expandable cage component 902 has a retracted, or compressed, state, and an expanded state. FIGS. 9A and 9D shows the expandable cage in the compressed state. Because the cage is porous, webbed, mesh-like or has openings, sensor 910 can function normally with the cage in the compressed state. Fibrin 908 may form over distal end 904 of the catheter as shown in FIG. 9B. The expandable cage component may be held in the compressed state by sleeve 906. When sleeve 906 is moved proximally with respect to the cage, the cage is allowed to expand to its natural expanded state as shown in FIG. 9C. Alternatively, the cage may be moved distally with respect to sleeve 906 to expand the cage. The opposite move is performed to collapse the cage.

Alternatively, cage 902 may be connected at its distal end to the distal end of the sensing catheter and at its proximal end to sleeve 906. In this embodiment, sleeve 906 is moved distally with respect to the sensing catheter (or the catheter is moved proximally with respect to the sleeve) to expand the cage. The opposite move is performed to collapse the cage.

The cage may be similar to a device called a stone retrieval basket used to retrieve kidney stones. The expansion of the cage may be performed manually or automatically. Alternatively, a canvas like material or a balloon may be used instead of the cage.

Figure 10A:
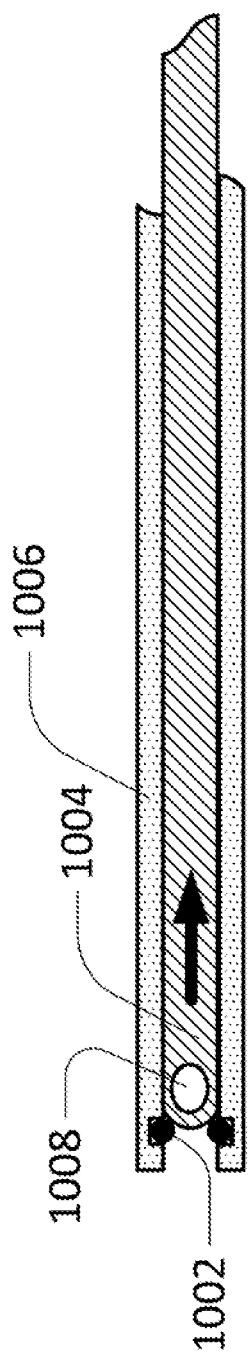
FIGS. 10A-10D show embodiments where the sensor assembly component includes an outer collar, or sleeve, over the sensor catheter assembly.
Figure 10B:
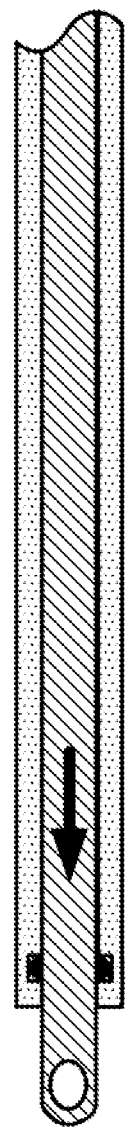
Figure 10C:
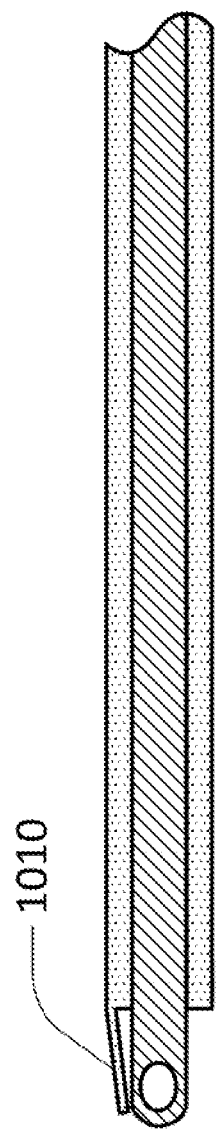
Figure 10D:
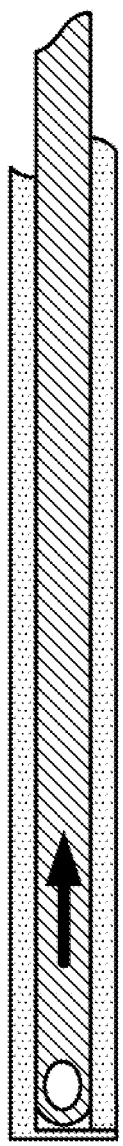

In the embodiments shown in FIGS. 10A-10D, the sensor assembly component may include an outer collar, or sleeve, over the sensor catheter assembly. Sleeve 1006 shields sensor 1008 and distal end 1004 of the catheter from encapsulation. The sensor may be extended outside of the sleeve when a measurement is required (e.g. once a minute), a measurement is taken, and the distal end of the sensor catheter assembly is retraced back within the sleeve. The sleeve incorporate a silicone membrane with a small hole, i.e. a sphincter, which expands as the sensor exits the collar. Alternatively, an O-ring may be used. FIGS. 10A and 10B show O-ring 1002. The sleeve may have a "trap door" that prevents fluid ingress during the time that the sensor is not active, and open to allow the sensor to exit the shroud. This opening could utilize spring force to open and close (spring, living hinge, etc.) and seal against the collar with an O-ring. Preferably, "trap door" 1010 is biased so that it is normally in the closed position, requiring a small amount of force to force it into the open position.

Figure 11:
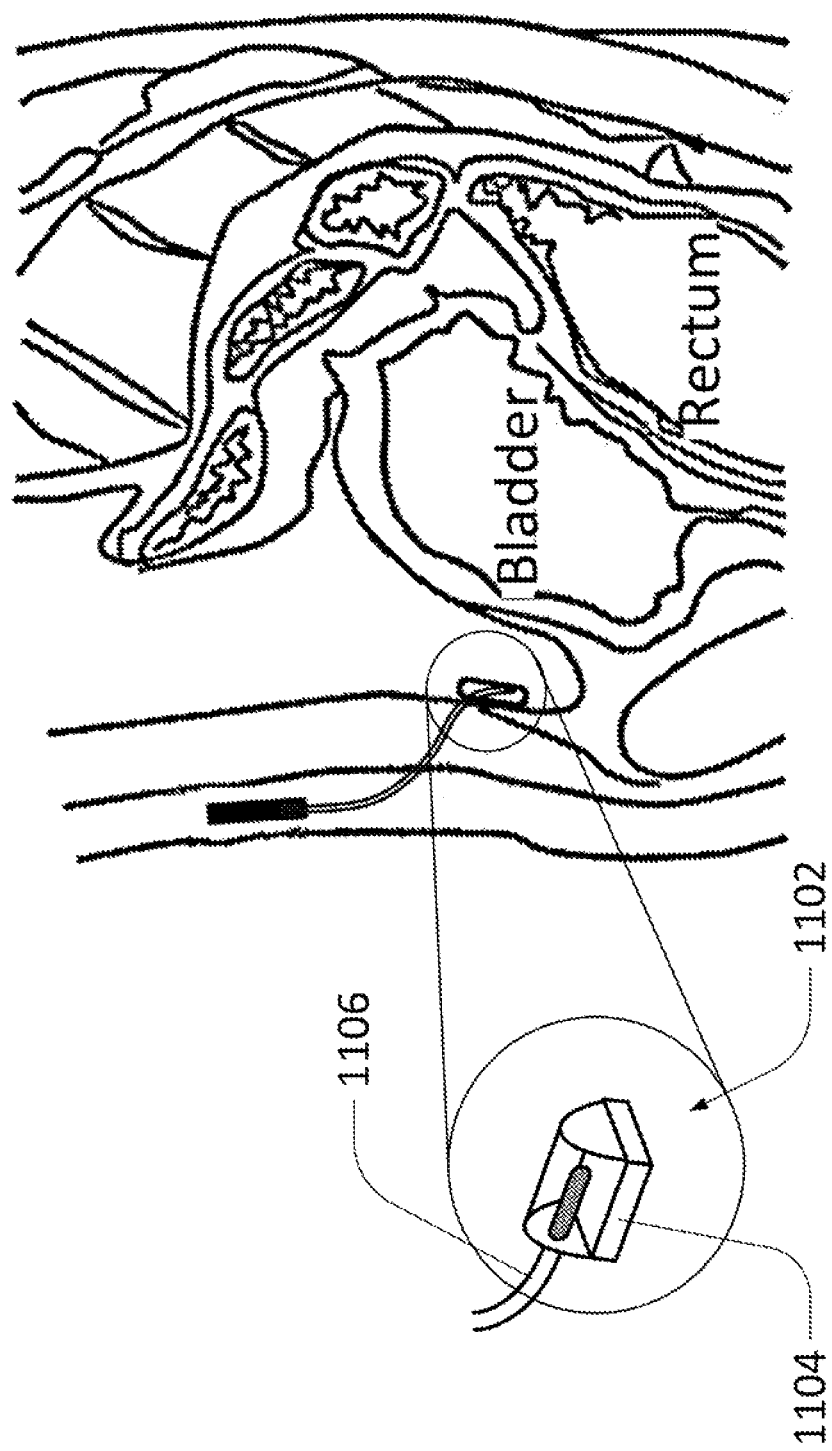
FIG. 11 shows an embodiment with a separately implantable "landing pad", or base structure.

Sensor location within the body affects the glucose readings acquired by the sensor component. Placing a free floating sensor in the peritoneal cavity has proven to show good results, however a more precise location would potentially increase accuracy and repeatability. A more precise location also may make it easier to swap out a sensor after a certain amount of time (e.g. 18 months). It is desirable to place a replacement sensor approximately same location as the replaced sensor to achieve repeatable results. In the embodiment shown in FIG. 11, separately implantable "landing pad", or base structure, 1102, is implanted into or onto a desired location of tissue (e.g., peritoneal lining, rectus sheath, etc) and becomes relatively permanently fixed to this region. The base structure may be manufactured all or in part from a material which allows tissue ingrowth (i.e. Dakron). For example, the base structure may include Dakron base component 1104. The base structure may have a collar, or marker, that a physician visualizes either by laparoscopy, x-ray, fluoroscopy, or ultrasound, so that he/she may guide sensor catheter assembly 1106 into or onto the base structure to fix the catheter in place.

The sensor component, in another embodiment, may be implanted in the fascia layer. Superficial, deep muscle, and visceral fascia are all possible sensor implantation sites. Tissue encapsulation of the sensor component may be less in these sites than in the peritoneal cavity. A glycol enzymatic sensor, or other sensor types disclosed herein, may be used in this area. In these embodiments, sensing technology that allows analyte containing tissue to contact the sensing element are preferable.

Figure 12:
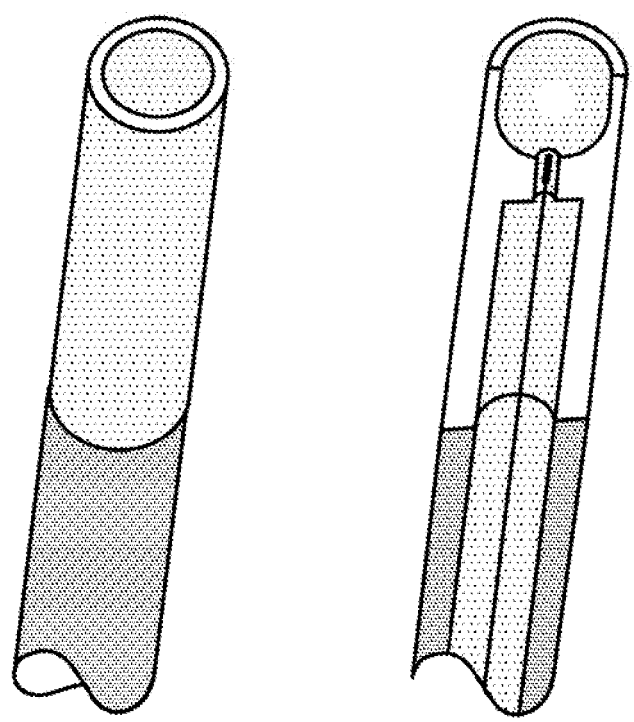
FIG. 12 shows an embodiment which includes a shroud, or cover, over the sensor.

Varying analyte concentrations in the local milieu may possible lead to erratic sensor readings. Some embodiments of the sensor assembly component may include a shroud, or cover, over the sensor with a piston style actuation on the proximal end of the catheter and/or sensor assembly. The piston draws fluid into the chamber during a reading, and subsequently expels the fluid when the reading is complete. This piston action would occur every time a reading is necessary (e.g. once a minute), i.e., the mechanism would draw in and expel fluid. This would ensure fluid is being cycled through, or across, the sensor properly, so that no stagnant fluid is left in or on the sensor. See FIG. 12.

In another embodiment of the control portion of the system, peritoneal fluid is drawn into a reservoir that's fully internalized which contains a sensor or an array of sensors to measure the glucose concentration of the fluid in the reservoir, or passing to/from the reservoir. The fluid may then be expelled or it may be recirculated. This embodiment may increases uniformity of glucose concentration from sample to sample. This reservoir may be rigid, or flexible (e.g. a balloon). The reservoir may be externalized and attached to the outside of the patient or be implanted, for example in the preperitoneal or subcutaneous space. The fluid may be analyzed using mid-infrared or near-infrared spectroscopy or other wavelength spectroscopy.

Sensors based on chemistry that require a fluorescing dye experience a phenomenon known as photobleaching, which is defined as the photochemical destruction of the dye molecule. Due to this phenomenon, a sensor of this chemistry will operate for a finite amount of time that depends on the time of exposure to the excitation source (LED, e.g.). Therefore, despite flushing or anti-encapsulation mechanism described herein, the sensor may still fail to respond after a certain amount of time due to destruction of the dye molecule. To address this problem, several approaches may be used.

Figure 13:
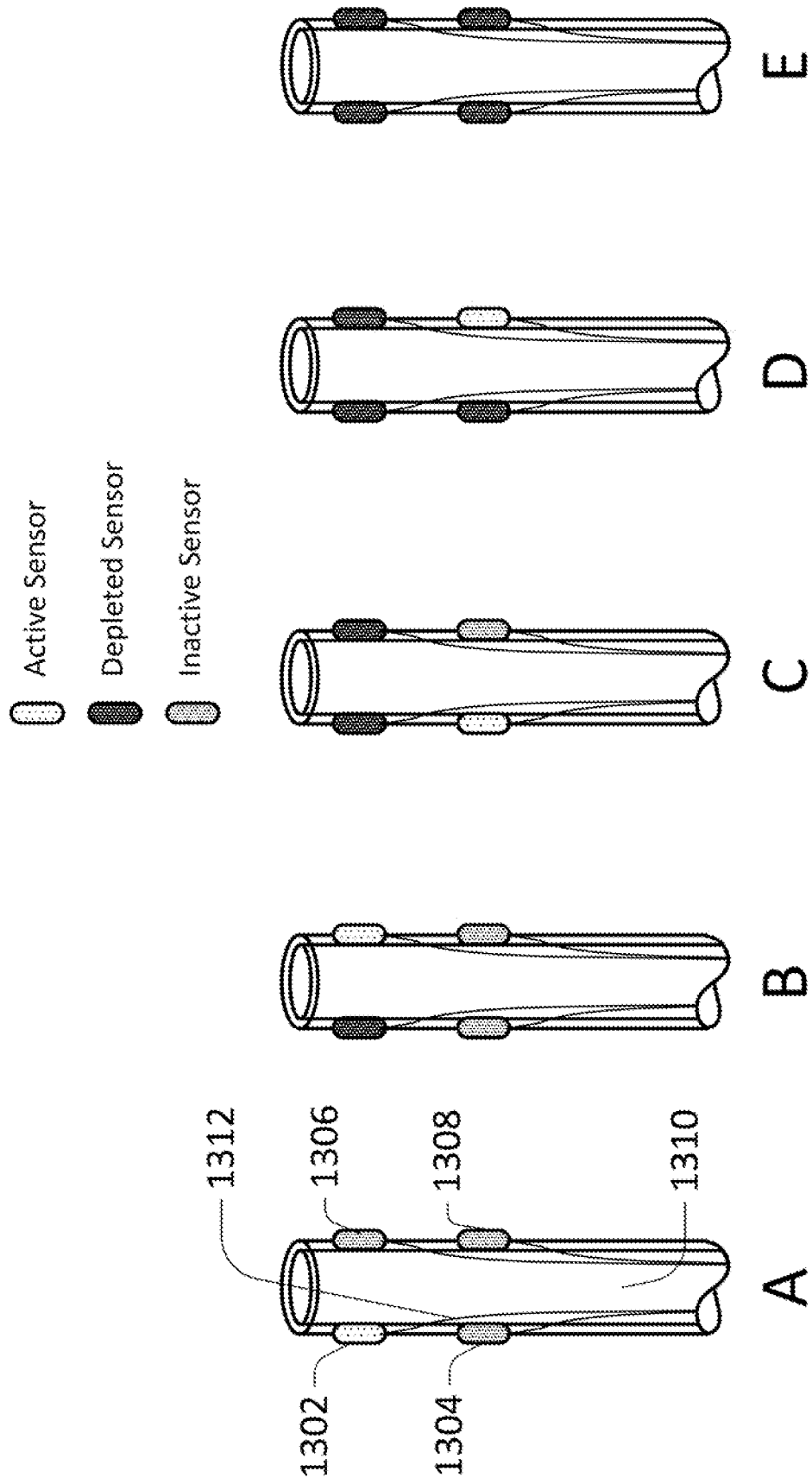
FIG. 13 shows an embodiment with multiple sensors.

In the embodiment shown in FIG. 13, multiple sensors are incorporated into one tube/catheter assembly, each sensor with its own fiber optic cable, and each sensor having its own excitation source. The catheter/tube, in this embodiment and other embodiments, may be manufactured from any suitable biocompatible and flexible material, including silicone, polyvinyl chloride, polyurethane, etc. In this embodiment, a primary sensor may be excited by its excitation source while the other sensors remain dormant. After either a set period of time and/or a set degradation in signal strength, the primary excitation source may cease operating, and a second excitation source would become active, exciting a second sensor. This process continues until each of the sensors in the assembly has been chemically depleted, or a set amount of time has passed. FIG. 13 shows multiple sensors 1302, 1304, 1306 and 1308 on catheter 1310. Fiber optic cable 1312 is connected to sensor 1302. Additional fiber optic cables are connected to the other sensors. In step A, sensor 1302 is active and sensors 1304, 1306 and 1308 are inactive. Once sensor 1302 becomes depleted, as is shown in step B, sensor 1306 becomes active, while sensors 1308 and 1304 remain inactive. In step C, both sensors 1302 and 1306 are depleted, and sensor 1304 is now active, leaving sensor 1308 inactive. In Step D, sensors 1302, 1304 and 1306 are all depleted and sensor 1308 is active. Finally, in step E, all 4 sensors are depleted.

A variation on this embodiment would be to excite each sensor in turn, until the entire sensor assembly is chemically depleted, rather than fully depleting each sensor before moving on to the next sensor. For example, if there are 4 sensing elements in the assembly, and measurements were taken once a minute, the operation would be as follows:

Minute 1: Excite sensing element #4
Minute 2: Excite sensing element #2
Minute 3: Excite sensing element #3
Minute 4: Excite sensing element #4
Minute 5: Excite sensing element #1
Etc.

Figure 14:
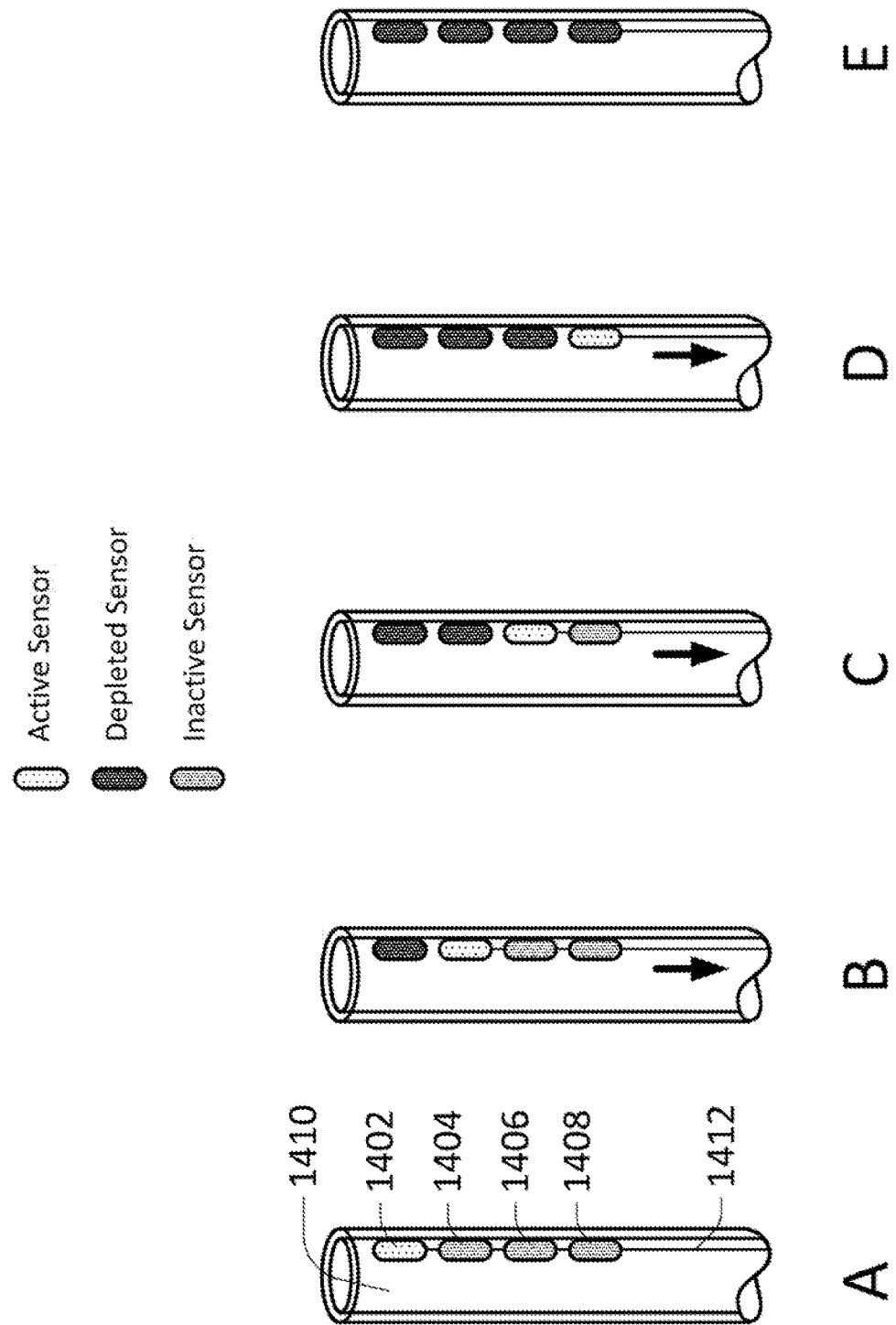
FIG. 14 shows an embodiment with an array of sensors.

In the embodiment shown in FIG. 14, an array of sensing elements is incorporated into a catheter as in the embodiments described above. However, one excitation source for all sensing elements, rather than a separate excitation source for each sensing element is used. Sensors 1402, 1404, 1406 and 1408 are shown on catheter assembly 1410. The excitation source is in communication with fiber optic cable 1412, Fiber optic cable 1412 can be moved with respect to the catheter assembly, so that its most distal tip may be in communication with one sensor at a time, and then moved to excite another sensor. In step A, distal most sensor 1402 is in communication with fiber optic cable 1412 and is active. Step B shows the assembly after the signal has degraded on most distal sensor 1402 (or after a set time has expired). Excitation source cable or connector 1412 is pulled back proximally, so that its distal tip is aligned with the next most proximal sensing element, sensor 1404, which is now active. The fiber optic cable may be fixed in place until it is moved again. This process continues until each of the sensors in the assembly has been chemically depleted, or a set amount of time has passed, as is shown in subsequent steps C, D and E. This assembly may be linear or it may be coiled.

Any feature of any embodiment disclosed herein may be combined with other features and/or embodiments. For example, a flushing mechanism could be combined with a wiper collar mechanism to ensure encapsulation could be cleared. A mesh network may also incorporate encapsulation clearing features at one, or more, sensor element to ensure proper functionality.

FIG. 15 shows an embodiment of the peritoneal sensor system which uses infrared, mid-infrared or near-infrared spectroscopy or other wavelength spectroscopy or spectrophotometry. Control portion 1502 is preferably implanted subcutaneously, but can be implanted anywhere as disclosed herein. The control portion may also be external as disclosed herein. catheter sensor portion 1504 is preferably placed so that the distal tip is in the peritoneal cavity, however the catheter/sensor portion may be placed anywhere as disclosed herein. in this embodiment, the sensor portion is a sensor interface which includes micro-dialysis membrane 1506. The micro-dialysis membrane is permeable to certain analytes (for example, glucose), but is impermeable to contaminates.

The target analyte/glucose passively diffuses across the membrane, from the fluids in the peritoneal cavity, into the sampling fluid which is circulating within sampling lumens 1508. In this embodiment, the sampling fluid is continuously, or intermittently, circulated through sampling lumens 1508, preferably in a closed loop system, but the fluid may alternatively be circulated in an open loop system. The sampling fluid may also be referred to as the "perfusate" or "dialysate". The sampling fluid may be sterilized and/or analyzed using light source/analyzer 1510 which shines light of particular wavelengths through the sampling lumen(s) and the sampling fluid to analyze the fluid for glucose content. Reflector 1512 may be utilized to reflect the light delivered from light source 1510 so that light source/analyzer 1510 may also be used to analyze the resulting light, after it has passed through the sampling fluid. Alternatively, the sampling fluid may be analyzed in a reservoir. The sampling fluid may alternatively include an antibiotic which is too large to pass through the membrane.

In this way, the sampling fluid is continuously, or intermittently, passing by micro-dialysis membrane 1506, where glucose diffuses into the sampling fluid, and the fluid containing the glucose is passed by light source/analyzer 1510 to collect data relating to glucose concentration. The glucose concentration within the sampling fluid reflects the glucose level within the patient. Sampling fluid pump 1514 may be used to circulate sampling fluid tier analysis. UV light may also be delivered from light source/analyzer 1510 to sterilize the sampling fluid or UV light may be delivered from a separate source.

In preferred embodiments, sampling lumen(s) 1508 are small to allow for quicker response times to changing glucose levels in the body and also to minimize trauma to the body. For example, the ID of the sampling lumen may be from about 0.2 mm to about 0.5 mm. Alternatively, the ID of the sampling lumen may be from about 0.5 mm to about 1.0 mm.

In a closed loop system, the glucose concentration in the sampling fluid will equilibrate with the glucose concentration in the body and reflect changes to glucose concentration in the body quickly as a result.

The sampling lumens may be next to each other, or coaxial, so one inside the other. The micro dialysis membrane may be tubular, so wrapping around 360 degrees of the catheter assembly, or it may only cover a portion of the circumference of the catheter assembly.

The sampling fluid within the sampling lumen(s) may be under slightly negative pressure.

The peritoneal sensor system shown in FIG. 15 also includes flushing lumen 1516. The flushing lumen is used to flush tissue and/or other contaminates from micro-dialysis membrane 1506. Flushing lumen 1516 may be annular, so surrounding the sampling lumen(s) or may be of any other shape. Any other flushing or dislodging mechanism disclosed herein may also be used. Flushing fluid may be forced distally using flushing pump 1518, or by any other means. Flushing fluid may be saline, may come from a replenishable reservoir, for example a self-sealing injection port, and/or may be peritoneal fluid which is drawn into either the flushing lumen, or a flushing fluid reservoir from the peritoneal cavity. Flushing fluid may contain insulin. In embodiments where the flushing fluid is peritoneal fluid, the fluid may enter the flushing reservoir by a slow reversal of flushing pump 1518, or the fluid may be allowed to leak or seep into the reservoir over time. In this situation the reservoir, or a port to the reservoir, may be porous or perforated, or permeable.

Insulin delivery lumen 1520 ending in insulin delivery opening 1522 may also be incorporated into the system. Insulin pump 1524 may draw insulin from insulin reservoir 1526 and deliver it to the patient via insulin delivery lumen 1520 and out insulin delivery opening 1522. The insulin delivery opening may be distanced from micro-dialysis membrane 1506 to prevent glucose measurement interference caused by the added insulin. Insulin may be replenished in insulin reservoir 1526 by penetrating a self-sealing port within the reservoir with a needle through the skin of the patient. The insulin reservoir may be external to control portion 1502 or may be internal to the control portion. The flushing reservoir may be external to control portion 1502 or may be internal to the control portion.

Control portion 1502 includes a controller which regulates the various systems in communication with the control portion. These systems include the various pumps, the light wavelength analysis mechanism, control of the insulin delivery based on glucose measurements via the wavelength analysis mechanism, flushing, etc. Control portion 1502 may also include wireless communication technology (transmitter and/or receiver) to communicate with an external controller which may be a computer, mobile phone, tablet or other device. The external controller may include a wireless receiver/transmitter as well.

The external controller may include a display communicating the status of the various systems to the patient and/or his doctor. These displays may include glucose level, including glucose level over time, glucose level graph, glucose level averages, glucose level warnings, glucose level changes etc. The display may also include insulin delivery volumes, insulin delivery changes, insulin delivery alarms, insulin level within the system etc.

The control portion will also contain a battery, or other source of power, and may be replenished through an electromagnetic field, inductive charging etc.

Other embodiments include an agitation mechanism which agitates and/or vibrates the sensor/sampling component to help keep the area clean and free of ingrowth.

In some embodiments, peritoneal fluid is drawn into the catheter, or circulated through the catheter, and passes by the filter membrane. In these embodiments, the filter membrane may be inside the controller, or in the central or proximal areas of the catheter. The sampling catheter may have one, two or more lumens.

In moving continuous glucose monitoring to the IP space, we must also consider the properties of the new sensing environment which is known to have less access to fluids. In same embodiments, the sensor design includes the addition of a biocompatible polymer layer to the sensor to improve contact with local fluids, mitigate contact of hydrogen peroxide with local tissue, and provide an opportunity to manipulate the rate of diffusion of oxygen and glucose to the sensor chemistry for optimal signal by controlling the formulation, cross-linking, and thickness of the polymer. To improve signal integrity over time and protect tissue from hydrogen peroxide production of the glucose oxidase reaction in vivo, these embodiments includes the addition of polymer layer to the sensor surface. Biopolymers have tunable diffusive properties with respect to two inputs of the glucose sensing reaction-oxygen and glucose. A polymer layer can therefore be used to control reaction rates. Polymer cross-linking ratio and/or thickness tolerance requirements are optimized to obtain ideal diffusive properties for the physiological range of glucose of interest. Polymer layer assembly is dependent on the type of polymer formulation applied. Some possible polymers include alginate, polydimethylsiloxane (PDMS), and other hydrogels, medical coatings, or thin film used by the medical device industry. Assuming formulation is consistent, diffusion of analytes through a polymer will be highly dependent upon thickness. Some embodiments mitigate variation in polymer thicknesses during manufacturing by calibrating signal against background signal using redundant sensors. Including a polymer layer will also mitigate inaccuracies emerging from an IP-implanted sensor which is not continuously submerged in a homogeneous fluid to sense glucose concentrations.

Polymer coatings are preferably biocompatible, durable in vivo, hydrophilic, and permeable to oxygen and glucose. An example of such polymer are biocompatible hydrogels which are typically composed of a two components, a polymer and cross-linker, the latter which is activated upon exposure to UV radiation. Hydrogels are often mixed within a mold and cured to form desired shape. The ratio of polymer to cross-linker, and exposure to UV radiation, can be used to control the density and mechanical structure of hydrogel polymers.

In one embodiment, the sensor assembly consists of 3-4 modified sensors assembled into a dual-lumen tube within a silicone tube catheter. Wire sensors may be attached to the silver and platinum electrodes Using conductive silver epoxy, and the joints may be encapsulated with insulating epoxy to prevent shorts due to fluid intrusion. Under clean conditions, sensors may be threaded down one lumen of the catheter. Proximal ends of the tubes are sealed and ports are bonded in line with each lumen to allow for flushing. The assembly may then be connected to the transmitter.

Lag times for blood glucose measurements in the IP space using the IP continuous glucose monitor may be less than around 12 min. Alternatively the lag times for blood glucose measurements in the IP space using the IP continuous glucose monitor may be less than around 10 min. Alternatively the lag times for blood glucose measurements in the IP space using the IP continuous glucose monitor may be less than around 7 min. Alternatively the lag times for blood glucose measurements in the IP space using the IP continuous glucose monitor may be less than around 5 mm.

In some embodiments, redundant sensors for glucose signal, background signal, and oxygen signal are included. Redundancies in sensors provides the algorithms with the data points required for calibration of glucose signal against background signal and oxygen tension during physiologic changes in the local environment. Calibration against background is well known in signal processing to improve accuracy and reduce noise of the target signal. It has been shown that adding redundant and reference sensors to a single device can improve accuracy by providing larger sample size over which signal can be averaged, a reference signal on background, and a reference signal on local fluctuations on environmental factors such perfusion, oxygenation, and encapsulation. One role of an oxygen sensor is to improve accuracy of glucose estimates by allowing algorithms to correct for small changes in oxygen tension which occur during physiologic changes. Another role of an oxygen sensor is to enable early-warning of peritonitis, the consequences of peritonitis are potentially severe, especially in immune compromised T1 OM patients. To mitigate this risk, the IP CGM device includes a proprietary algorithm for use in implantable devices which provides early indication of an infection based on combined oxygen/glucose sensor readings.

Some embodiments include a wearable receiver display in wireless communication with a fully implanted sensor and transmitter.

Example of Data Processing System

Figure 17:
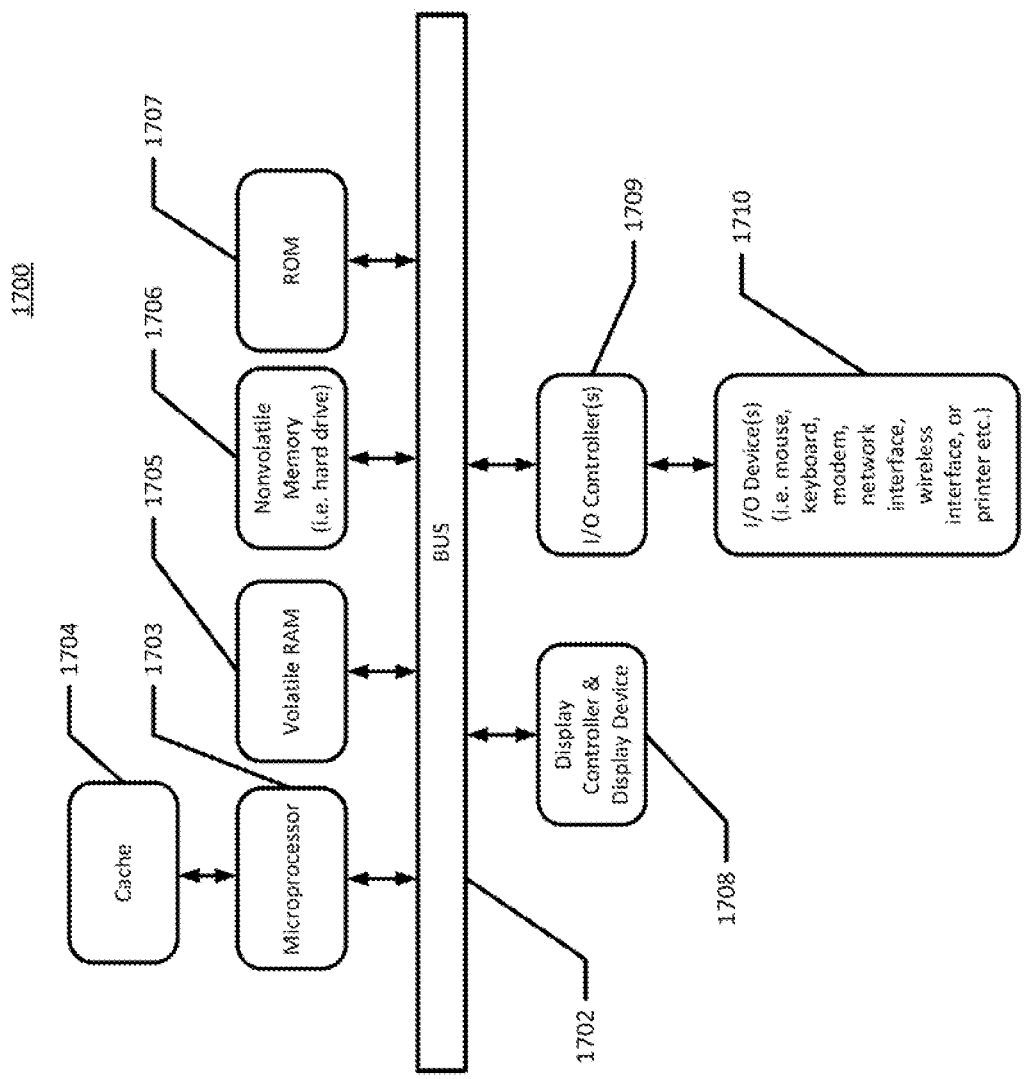
FIG. 17 shows a block diagram of a data processing system, which may be used with any embodiments of the invention.

FIG. 17 is a block diagram of a data processing system, which may be used with any embodiment of the invention. For example, the system 1700 may be used as part of the control component of the peritoneal sensing system. Note that while FIG. 17 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 17, the computer system 1700, which is a form of a data processing system, includes a bus or interconnect 1702 which is coupled to one or more microprocessors 1703 and a ROM 1707, a volatile RAM 1705, and a non-volatile memory 1706. The microprocessor 1703 is coupled to cache memory 1704. The bus 1702 interconnects these various components together and also interconnects these components 1703, 1707, 1705, and 1706 to a display controller and display device 1708, as well as to input/output (I/O) devices 1710, which may be mice, keyboards, modems, network interfaces, printers, and other devices which are well-known in the art.

Typically, the input/output devices 1710 are coupled to the system through input/output controllers 1709. The volatile RAM 1705 is typically implemented as dynamic RAM (DRAM) which requires power continuously in order to refresh or maintain the data in the memory. The non-volatile memory 1706 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 17 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1702 may include one or more buses connected to each other through various bridges, controllers, and/or adapters, as is well-known in the art. In one embodiment, the I/O controller 1709 includes a USB (Universal Serial Bus) adapter for controlling USB peripherals. Alternatively, I/O controller 1709 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the Operations described may be performed in a different order. Moreover, some operations may be performed in parallel rather than sequentially.

What is claimed is:

1. A peritoneal fluid sensing apparatus, comprising:
   a catheter having a distal tip and defining a sampling lumen and a flushing lumen each at least partially through the catheter;
   a sensor configured to sense for a presence of one or more analytes when contacting peritoneal fluid of a subject;
   a controller in communication with the sensor, wherein the sensor is positioned within the controller;
   a filter positioned at or near the distal tip of the catheter and in fluid communication with the sensor, wherein the filter is permeable to the one or more analytes; and
   a port in fluid communication with the flushing lumen at least partially through the catheter and the sensor such that infusion of a fluid through the port flushes the filter at or near the distal tip with the fluid.

2. The apparatus of claim 1 wherein the controller is configured to receive sensed information from the sensor and determine a glucose level within the peritoneal fluid.

3. The apparatus of claim 2 wherein the controller is further configured to infuse insulin based on the determined glucose level.

4. The apparatus of claim 1 wherein the analyte comprises glucose.

5. The apparatus of claim 1 further comprising a sleeve or cuff sized to slidingly receive the catheter therethrough.

6. The apparatus of claim 5 further comprising an anchoring cuff or tunnel positioned along the catheter or sleeve and configured to promote tissue ingrowth.

7. The apparatus of claim 1 wherein the controller is located remotely from a second sensor.

8. The apparatus of claim 1 wherein the controller is configured to automatically infuse the fluid into the port to intermittently flush the sensor.

9. The apparatus of claim 1 wherein the fluid comprises insulin, saline, peritoneal fluid, or combinations thereof.

10. The apparatus of claim 1 further comprising a pump in fluid communication with the catheter and in electrical communication with the controller.

11. The apparatus of claim 10 further comprising a fluid reservoir in fluid communication with the pump.

12. The apparatus of claim 1 wherein the tip of the catheter is made from a material which inhibits cell ingrowth.

13. The apparatus of claim 1 wherein the controller further includes a sterilization element.

14. The apparatus of claim 13 wherein the sterilization element comprises an ultraviolet light source.

15. The apparatus of claim 1 wherein the controller is in fluid communication with the fluid.

16. The apparatus of claim 1 wherein the filter is comprised of a permeable membrane.

17. The apparatus of claim 1 wherein the filter is positioned within the catheter.

18. The apparatus of claim 1 wherein the sensor is configured for light spectroscopy.

\* \* \* \* \*